(12) United States Patent
Lo

(10) Patent No.: US 7,094,371 B2
(45) Date of Patent: Aug. 22, 2006

(54) POROUS SYNTHETIC BONE GRAFT AND METHOD OF MANUFACTURE THEREOF

(75) Inventor: Wei Jen Lo, Nottingham (GB)

(73) Assignee: Orthogem Limited, Wollaton (GB)

(\*) Notice: Subject to any disclaimer, the term of this patent is extended or adjusted under 35 U.S.C. 154(b) by 343 days.

(21) Appl. No.: 10/343,482

(22) PCT Filed: Jul. 27, 2001

(86) PCT No.: PCT/GB01/03397

§ 371 (c)(1),
(2), (4) Date: May 9, 2003

(87) PCT Pub. No.: WO02/11781

PCT Pub. Date: Feb. 14, 2002

(65) Prior Publication Data

US 2003/0171822 A1    Sep. 11, 2003

(30) Foreign Application Priority Data

Aug. 4, 2000   (GB) ................................ 0019003.3
Dec. 12, 2000  (GB) ................................ 0030295.0

(51) Int. Cl.
*B29C 44/02* (2006.01)
(52) U.S. Cl. ............................ 264/28; 264/42; 264/54; 264/108
(58) Field of Classification Search .................. 264/44, 264/54, 108, 28, 42, 49; 623/16.11
See application file for complete search history.

(56) References Cited

U.S. PATENT DOCUMENTS

| 4,073,999 A | 2/1978 | Bryan et al. |
| 4,973,566 A | 11/1990 | Readey et al. |
| 5,278,007 A | 1/1994 | Nanataki et al. |
| 5,549,123 A * | 8/1996 | Okuyama et al. ........... 128/898 |
| 5,705,118 A | 1/1998 | Hayes et al. |
| 5,958,314 A * | 9/1999 | Draenert ..................... 264/42 |
| 6,511,510 B1 | 1/2003 | de Bruijn et al. |
| 2002/0035402 A1 | 3/2002 | de Bruijn et al. |
| 2002/0037799 A1 | 3/2002 | Li et al. |

FOREIGN PATENT DOCUMENTS

| EP | 335359 A2 | 10/1989 |
| WO | WO 01/44141 | 6/2001 |
| WO | WO 02/066693 | 8/2002 |

\* cited by examiner

*Primary Examiner*—Allan R. Kuhns
(74) *Attorney, Agent, or Firm*—Quarles & Brady LLP

(57) ABSTRACT

A process for preparing artificial bone is described which comprises: (i) preparing a mixture of a finely divided bio-compatible ceramic powder, an organic binder and a pore-forming agent in an inert liquid to form a body and causing at least some of the pore-forming agent to align along a common axis; (ii) optionally shaping the resulting body; (iii) allowing the pore-forming agent to form a porous structure in the body; (iv) heating the shaped body to a temperature sufficient to fix the porous structure and; (v) further heating the body to eliminate residues of organic binder and pore-forming agent and to fuse it.

22 Claims, 2 Drawing Sheets

POROUS SYNTHETIC BONE GRAFT AND METHOD OF MANUFACTURE THEREOF

This application claims priority on GB0019003.3 filed on Aug. 4, 2000, GB0030295.0 filed on Dec. 12, 2000, as well as PCT/GB01/03397 filed on Jul. 27, 2001.

This invention relates to the fabrication of synthetic bone in the form of a porous block from calcium phosphate or other ceramic powder. More particularly, this invention relates to a new manufacturing process to create a good synthetic bone graft with a controllable porous structure. It can be used to replace the autograft and allograft for orthopaedic surgeries including vertebrae repair, musculoskeletal reconstruction, fracture repair, hip and knee reconstruction, osseous augmentation procedures and oral/maxileofacial surgery.

Currently the European bone graft market is dominated by autograft (bone taken from one part of the body and transferred to another part of the same individual) and allograft (bone taken from one individual and transferred to a different individual). In an autograft procedure, the bone grafts are taken from the patient, typically the pelvis. Two operations have to be done simultaneously. The patient benefits from having compatible, living cells at work in the defect area. However, the drawbacks can be significant. Among them are chronic, often debilitating pain that results from the harvesting operation, blood loss, risk of infection, and longer hospital stay and recovery time. The second surgery also adds substantially to the financial cost.

An allograft procedure usually uses bone from a cadaver. While this eliminates the need for a second surgical procedure, the grafted bone may be incompatible with the host bone and ultimately rejected. Allograft also poses a slight but troubling risk of introducing a variety of viruses, including those that cause AIDS or hepatitis, into the patient. Therefore, many efforts have been made to develop biocompatible, synthetic bone graft.

BACKGROUND OF INVENTION

Commercially available synthetic bone grafts are usually made of calcium phosphate ceramics (the main inorganic materials of human bone) and have a porous structure similar to the human cancellous bone. Many of them are actually derived from animal (young bovine) or marine (sea coral) life. They are intended to offer an interconnected macroporous structure and provide intensive osteoconductivity to regenerate and heal the host bone tissue. However, none of them offer the biomechanical and osteointergrative properties equivalent to the gold standard of autograft.

These synthetic bone grafts usually come with an interconnected macroporous structure, typically of 100~500 μm diameter, which provides a framework for the host bone to regenerate while reducing healing time. The pore size of the porous structure is crucial for the osteoconductivity. According to the in vitro and in vivo experiments, the proper pore size for bone tissue ingrowth is around 200~300 μm. If the pore sizes are smaller than 100 μm the bone tissue may accumulate on the surface without osteoingrowth. After the implant, the bone graft should be slowly degraded and replaced by the growing bone. It should result in bone replacement at the site of defective bone by the recipient's own osteogenic activity. However, degradation requires the bone substitute materials to be microporous, with pore diameter from 1~5 μm. The dissolution process of the "degradable" bone graft occurs in two steps: extracellular dissolution of the necks among sinterized particles, and intracellular phagocytosis of the particles isolated in this way. The first step becomes impossible in annealed bioceramics bulk and very difficult in those porous synthetic bone grafts with a thick connected wall because there are no small necks that the cells can attack.

Commercially available synthetic bone grafts usually have a random distribution of pore sizes and no observable preferred orientation of the inter-connected porous structure. The structure has the potential to prevent vascularisation after a period of time in vivo and the middle of the bone graft usually remains bone free. Although most of the commercial bone grafts have a similar chemical composition to the mineral phase of the living bone, the graft is not suitable for large scale application or as the permanent replacement since nutrients cannot flow through the synthetic porous bone graft after the surgery.

THE INVENTION

The present invention provides a novel manufacturing process which produces a unique and extremely flexible porous structure. No biological materials need be involved in the final product. It can mimic humane cancellous bone in large scale and the pore size can be varied from a few microns to several millimetres. The process allows a controllable pore size, shape and pore orientation. Numerous, various sized interconnected tube-like pores (with preferred orientation) can be provided to guide osteoingrowth and vascularisation swiftly through the whole structure. The porous structure can have a thin wall making it easier for osteoblasts to attach to and stimulate mineralization. The size and shape of the bone graft can be adjusted by a moulding process, for example, or can be shaped by the orthopaedic surgeon during the operation by tools such as a diamond wheel or high-speed drill.

According to the present invention there is provided a process for preparing artificial bone which comprises:
  (i) preparing a mixture of a finely divided bio-compatible ceramic powder, an organic binder and a pore-forming agent in an inert liquid to form a body and causing at least some of the pore forming agent to align along a common axis,
  (ii) optionally shaping the resulting body,
  (iii) allowing the pore-forming agent to form a porous structure in the body,
  (iv) heating the shaped body to a temperature sufficient to fix the porous structure and
  (v) further heating the body to eliminate residues of organic binder and pore-forming agent and to fuse it.

DETAILED DESCRIPTION OF THE INVENTION

Figure 1:
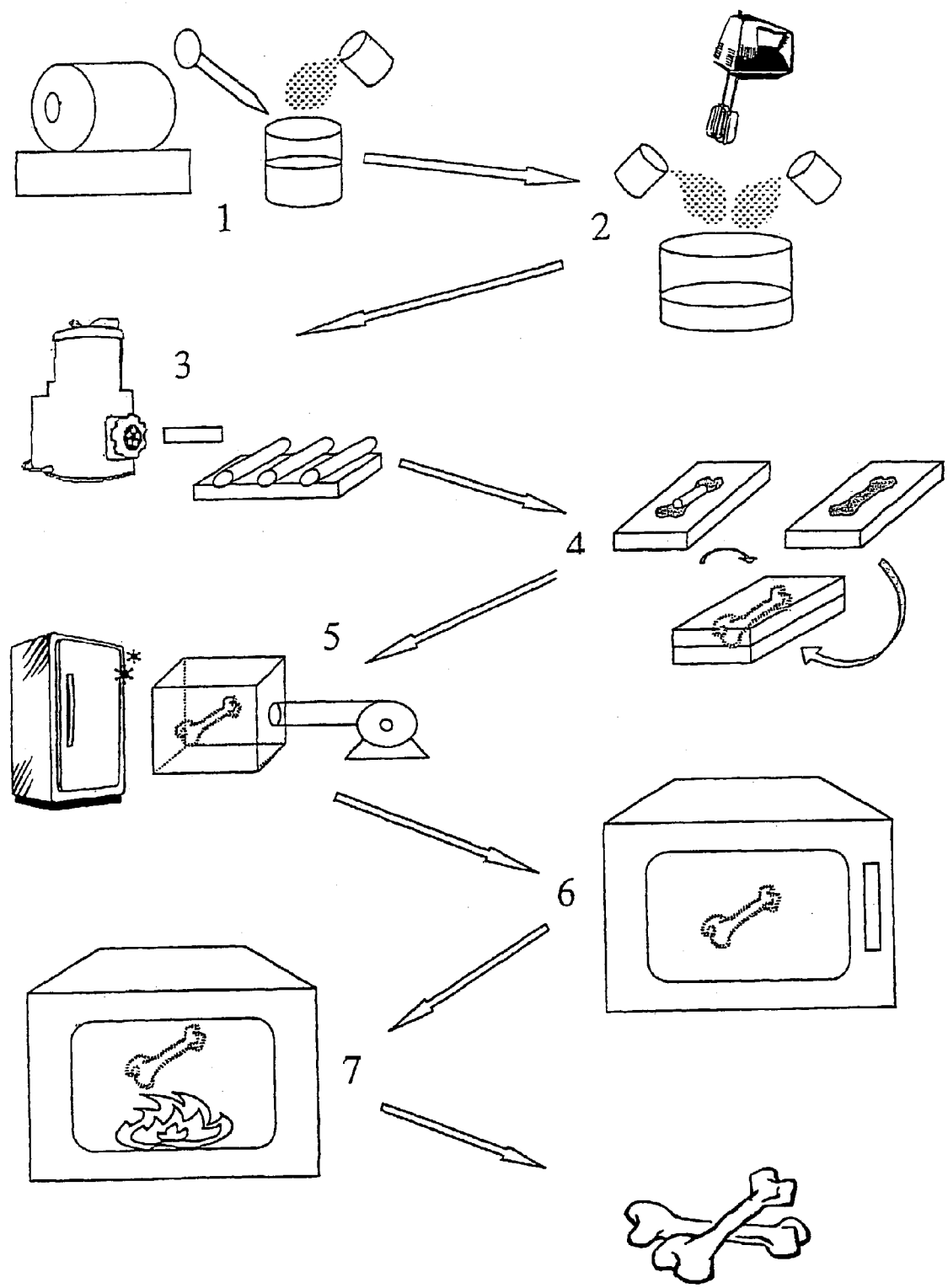
FIG. 1 is a schematic view of a process of the present invention.

Having described the invention in general terms, it will now be described with reference to the accompanying drawing in which the Figure shows a flow chart of a typical process of this invention.

The essential ingredients of the process are the biocompatible ceramic powder, the organic binder and the pore-forming agent. The ceramic powder can be any ceramic material which is bio-compatible. For example it can be a mechanical ceramic in order that the resulting artificial bone graft possesses the sufficient strength. Materials which can be used include zirconia and alumina. It is, however, preferred to use a calcium phosphate ceramic. While all medical grades of tricalcium phosphate including α-tricalciumphosphate (TCP), β-TCP and hydroxy apatite (HA) $Ca_{10}(PO_4)_6(OH)_2$ can be used for this purpose, it is preferred to use HA for large scale work as it is more stable. Mixtures of bio-compatible materials can be used, for example mixtures of calcium phosphate ceramic and alumina or zirconia. In addition small amounts of silica and an organic zinc compound, for example up to 5% by weight, can be incorporated in the powder to increase its osteoconductivity.

It is preferred that the ceramic powder is dispersed homogeneously. The smaller the particle the larger the surface area and hence the tendency of a particle to be wetted by the liquid; this also facilitates the final sintering. Generally, the powder does not exceed an average diameter of about 100 microns. Thus preferred powders will have an average particle diameter from 1 nm to, say, 50 microns, for example from 0.1 to 10 microns.

The organic binder has to bind the ceramic powder together to form a closely packed structure with many points of contact between each ceramic particle with gaps at the interstices where the inert liquid remains. The precise nature of the organic binder is not critical provided that it does not leave a residue on firing; it will generally be solid. It has been found that carbohydrate powders are particularly useful especially cornflour or wheat flour but other organic materials such as naturally extracted starch can be used. One of skill in the art will appreciate what alternative materials could be used. The binder should be incorporated into the slurry as a powder.

The pore-forming agent is present in order to form pores in the body formed from the ceramic powder and binder. This is generally achieved by the evolution of gas from the pore-forming agent. Suitable pore-forming agents include micro-organisms such as fungi eg. yeast cells, along with inorganic salts of acids derived from phosphorus and carbon, especially alkali metal salts, such as sodium salts, of phosphates and carbonates. Specific examples include disodium diphosphate and sodium bicarbonate.

The slurry is formed in an inert liquid i.e. the liquid must not react with the pore-forming agent at room temperature nor react with the ceramic binder. Typically, the inert liquid is water, especially de-ionised water although an organic liquid such as ethanol can also be used.

In a preferred embodiment of step (i) a slurry of the ceramic powder is first prepared and then the organic binder and pore-forming agent are added to it (steps 1 and 2 in the Figure). However, the ceramic powder, organic binder and pore-forming agent can also be mixed together and then the liquid solvent added. In a preferred embodiment a calcium phosphate ceramic slurry is first prepared by mixing the calcium phosphate with the water or other inert liquid. In order to aid dispersion, it is preferred to add a dispersing agent to ensure that the ceramic powder is uniformly distributed throughout the slurry. Typical dispersing agents which can be used for this purpose include acid/base solutions and polymers such as phosphates and acrylate polymers. Preferred dispersing agents include ammonia, phosphoric acids such as orthophosphoric acid or an ammonium salt of an acrylate or methacrylate polymer such as ammonium polyacrylate and ammonium polymethacrylate.

It is then preferred to mill the slurry, optionally with milling media such as beads or cylinders of alumina, stainless steel or tungsten carbide. These milling media are, of course, removed following milling.

In a preferred embodiment, milling is carried out in a cylinder miller, typically rubber walled. Usually the sealed cylinder miller is allowed to rotate at low speed for several hours to form a high density and well dispersed ceramic slurry. It is generally preferred for the milling operation to take at least 1 hour up to say, 50 hours, in order to optimise the size of the powder. It will be appreciated that the size of the powder in the slurry can determine the size of the pores since the porous structure is, in effect, a series of compact irregular ceramic particles which are fused to their neighbours during the final step of the process.

Generally, thereafter, the carbohydrate powder and pore-forming agent are gradually added to the slurry to form what might be described as a high viscosity elastic material. It is preferred that the mixing is performed in a sealed oxygen chamber to ensure that the mixed materials are oxygen rich for the pore-forming agent to react. It will be appreciated that the quantity of the binder determines the elastic properties of the mixture while the amount of pore-forming agent controls the total porosity of the final product.

It will also be appreciated that the precise conditions used in step (iii) will depend on the nature of the pore-forming agent. Thus if yeast is used it is generally necessary for a source of a nutrient to be present such as a small amount of sugar to stimulate the metabolism to generate carbon dioxide. Generally raising the temperature of the body will cause the pore-forming agent to react, resulting in gas evolution. The pore-forming step can be accelerated by increasing the temperature and/or the pressure but it will be appreciated that care should be exercised to ensure that the temperature is kept below that at which the yeast will be killed. Generally, a temperature of 28 to 30° C. will cause the yeast to form pores. However it has been found that higher temperatures can be tolerated eg. up to 40° C. if a larger amount of yeast is used—some of it remains alive. Pore size is largely dictated by temperature and the amount of pore-forming agent used. The use of a sealed oxygen chamber assists the reproducibility of the process although, of course, mixing can be carried out simply in air.

The quantity of ceramic powder used should generally be as high as possible. Typically, one uses 80% total weight of ceramic powder, 19% of carbohydrate and about 1% of yeast. Generally, therefore, one uses 50 to 90% by weight of ceramic, 5 to 50% by weight of binder and 0.5 to 5% by weight, preferably 0.5 to 3% by weight of the pore-forming agent. Obviously, the precise quantities of pore-forming agent used depends of the nature of the agent.

It will also be appreciated that with time, providing there is sufficient pore-forming agent present, the size of the pores will increase. Ideally, the pore size should be about 200 to 300 microns. If the pore size is significantly smaller than this then there may not be sufficient for the osteoblast cells to ingrow. Further, if it is desired to fill the pores in any way, as discussed below, they should be slightly larger than the ideal pore size since otherwise the molecules will not be retained by the pores.

It will be appreciated that the body takes a dough-like appearance at this stage i.e. it holds its shape.

Preferably before the optional shaping step (ii) the product is transferred to an extruder or other device to provide the necessary shape and size for the shaping step (step 3 in the Figure). The aim of the extrusion step is to produce the desired pore shape and orientation in the final porous structure. By using different extrusion forces and different shapes of the front mould, the material can be formed into any geometrical shape with the desired alignment such as linear in either the vertical or horizontal plane, hollow tube, cross-link matrix or spiral form of the pores. It will be appreciated that the pore-forming agent will extend along the extrusion direction and ultimately create the desired pore orientation i.e. align along a common axis. Clearly, the body must have a sufficient viscosity as in a dough-like body for this alignment to be possible. Sometimes this can be achieved simply by stretching. It will be appreciated that a particular advantage in using a micro-organism that well connected pores can be formed. In contrast chemical agents generally give rise to pores which are not well connected.

Although the extrusion step is not essential to produce mimic cancellous or cortical bone structure, it is generally necessary if the artificial bone grafts are to be used in load bearing application. This is because the mineral composition of the nature load bearing bone, such as the femur and hip joint, possesses a tube-like structure rather than a simple cancellous bone structure. The orientation of this tube-like porous structure will follow in the loading stress distribution, which results in the load bearing bone being stronger than the bone in a rib.

The mixture is then optionally shaped (step 4 in the Figure). Preferably, it is shaped in a mould which is preferably sealed. The three dimensional shape of the mould can be designed with computer aided medical imaging analysis techniques so that the shape can replicate the patient's missing bone structure. Once the body has been sealed in the mould the temperature of the mould can be raised in order to allow the pore-forming agent to react and form the pores. It will be appreciated that the force caused by the expansion of the pore-forming agent compresses the mass of the ceramic powder. The amount of pore-forming agent along with the processing time and processing temperature determines the porous density and mechanical strength of the final product. The total time required at the optimised processing temperature to complete the reaction is typically from 30 to 90 minutes, preferably 40 to 60 minutes, especially about 45 minutes, depending on the size of the body.

Before step (iv) it is preferred to reduce the temperature of the body below the freezing point of the water if water is used as the inert liquid (step 5 in the Figure). Preferably, the sealed mould is reduced to a temperature of about −5° C. to the temperature of liquid nitrogen. The freezing step can prevent the pore-forming agent from reacting further. The expansion which results from the formation of ice from water further enhances the porous structure of the body. The frozen sample can then be removed from the mould.

It is generally necessary then to remove part of the liquid from the body, typically by evaporation. This can be achieved in a vacuum chamber during which the water or other liquid evaporates from the surface and the hydrostatic pressure gradients across the compact provide a driving force for the liquid to move. The liquid flows from the interior of the body to the surface through the porous channels thereby producing a more uniform pressure. Naturally, the processing temperature, rate of increase in temperature, the vacuum pressure and the duration of the sublimation process depend on the size and shape of the body and the nature of the liquid being employed. These can be determined by routine experimentation.

The aim of step (iv) is to stabilise the article (step 6 in the Figure). For this purpose, it is generally desirable to pre-heat the atmosphere (which can be dry or wet) in which the article is placed, typically an oven which is preferably humidity controlled. A temperature of, say, 100, 130 or 150 to 230° C. is generally suitable for stabilisation. Generally stabilisation can be achieved in less than 1 hour, generally 5 to 50 minutes, for example 15 to 45 minutes. It has been found that the use of steam is advantageous since it generally causes polymerisation of the organic binder without microcracks forming on the sample's surface which can be caused by direct heating processes. These cracks may remain and deepen during the further annealing processes and can therefore greatly reduce productivity.

Once the body has been stabilised it can, if desired, be machined to remove any uneven flashing and/or to adjust the final geometric form of the article so that it corresponds to the desired shape of the artificial bone graft.

In step (v) the article is heated or fired to eliminate the binder and any remaining pore-forming agent. Generally a temperature from 400° C. to 1000° C. is necessary for this purpose. This does, though, depend to some extent on the amount of binder used and on the heating rate applied. Since this heating step typically results in carbon-containing gases to be developed it will be appreciated that heating should be carried out slowly to allow these gases to diffuse out of the artificial bone through the interconnecting porous channels. If this is not done then the entrapped gas could build up a pressure sufficient to cause internal damage to the compact porous structure. Generally, the rate of heating should not exceed 10° C. per minute, typically not more than 5° C. per minute and perhaps as little as 1 or 2° C. per minute for a large sample.

The step of eliminating the binder is generally complete when no more carbon gases can be seen coming out of the article.

Preferably, following this heating step the sample is then annealed or sintered at a higher temperature, typically from about 1200 to about 1450° C., to achieve the necessary biomechanical strength and biocompatibility (step 7 in the Figure). Again, the temperature and duration of the heating depend on the size of the sample and the initial ceramic concentration. Care should be taken not to use too high a temperature since this can cause fusion of the small interconnected pores with the result that the macropores start to be isolated.

In some cases the product, although strong enough for some purposes, is insufficiently strong for others. It has been found that the strength of the product can be enhanced by immersing it in a ceramic slurry formed of ceramic powder, typically apatite, although it need not necessarily be the same as that used initially. The slurry should also contain a dispersion agent which can be the same as, or different from, that used initially. Desirably the slurry should be milled before use so as to reduce the particle size, for example from an average of 5 μm to an average of 1 μm. The slurry can be allowed to rest for, say, for 1½ hours to allow for the large particles to precipitate. Suitable particles with an average size of, say, less than 0.2 μm can be poured off from the suspension formed.

The immersion should typically lasts at least 0.5 hour with constant stirring of the slurry. After this, the slurry is desirably brought to boiling until no more air bubbles come out of the sample. This typically takes 10 minutes to 1 hour, depending on the size of the sample. This process ensures the micropores of the sample are packed with apatite particles. Any excess slurry and apatite particles can be removed by a centrifuge process (e.g. from 2500 to 15000 rpm) through the interconnected macroporous structure.

This immersion step can be repeated if necessary. Afterwards the sample can be subjected to the annealing step again.

Another way to improve the mechanical strength of the porous structure is to reinforce it with polymer, preferably a biodegradable polymer such as polycaprolactone (PCL); the polymer acts as a filler. For this purpose the polymer is dissolved in a solvent to provide a concentration of, say, 10 to 50% typically 20 to 40% by weight and then the body is immersed in it for, say, 5 min to 1 hour, e.g. 20 minutes. The body is then removed and centrifuged to remove any excess solution. It may be desirable then to heat the samples to cause any polymer blocking the pores to melt. This procedure can be repeated if desired.

In an advantageous embodiment of the present invention some or all of the pores of the artificial bone can be used as a drug delivery system with a controlled release mechanism. This can be achieved generally by immersing the artificial bone in a solution of the desired cell growth factors or drug.

At present, there is no effective drug delivery mechanism to deliver engineered high molecular weight proteins or enzymes into the bone. In accordance with the present invention this can be achieved because the size of the bone graft can be adjusted to accommodate the molecule. Thus high molecular weight engineered proteins or enzymes incorporated in this way can be released from the bone graft to stimulate osteoingrowth and the porous matrix can guide the osteoblast cells to proliferation and differentiation. Thus growth factors for osteoingrowth including transforming growth factor (TGF-β1), bone morpho genetic protein (BMP-2) and osteogenic protein (OP-1) can be incorporated into the artificial bone of the present invention in this way.

Other materials which can be incorporated include vitamins such as vitamin D and trace minerals such as zinc which can be incorporated in the form of a salt.

In a preferred embodiment, these molecules can be incorporated into the pores together with a biodegradable polymer. The biodegradable polymer helps to "fix" the active molecule in the pores while, at the same time, improving the strength of the artificial bone.

Suitable biodegradable polymers which can be used for this purpose include starch, typically corn starch, or other naturally occurring polymers or mixtures of such polymers with, for example, polyethylene or poly(lactic acid) or poly(glycolic acid). Generally, the concentration of non-naturally occurring should be kept low to avoid any possible adverse biological effects. It is, though, possible to use a mixture of starch and up to, say, 50% by weight of low density polyethylene.

The active compound, and biodegradable polymer if used, can be applied from a solution of the materials by immersion. The application of a slight vacuum to the artificial bone graft can be useful as it increases the uptake of the solution.

If one carries out this immersion step several times, the strength of the artificial bone can be increased quite significantly. Excess biodegradable polymer can generally be removed by centrifuging.

It will be appreciated, therefore, that the artificial bone graft of the present invention can be used as a 3-D scaffold for in vitro tissue engineered autografts.

The manufacturing cost of the process is generally significantly lower than existing processes and the manufacturing time is generally quicker than the other methods. In normal circumstances even a large scale specimen with an irregular shape can be produced in less than 24 hours. Therefore, it can be made to order. For example, before the maxillofacial operation the desired shape of the bone graft can be created according to the patient's 3-D skeleton scanning image. Therefore the bone graft can be produced individually for each patient.

The following Examples are illustrative of the invention.

EXAMPLE 1

Commercial medical grade hydroxy apatite $Ca_{10}(PO_4)_6(OH)_2$ powder(ASTM F118588), particle size from 0.6 μm to 1 μm, was used to produce the synthetic porous bone graft. The first step is to make a slurry where the ingredients are:

160 grams of hydroxy apatite powder
70 millilitres of de-ionised water
2 grams of ammonium polyacrylate.

These ingredients were initially homogeneously mixed in a plastic container with a spatula. When a uniform solution had been formed, mechanical agitation was applied with a double-bladed stirrer at approximately 1200 rpm for 5 minutes. This made approximately 115 ml of slurry. The slurry was then poured into a cylinder miller for further dispersion of the agglomerates; this was a polyethylene flask, 10 cm long and 6 cm diameter, containing 100 cm³ of high-density small $Al_2O_3$ cylinders. The cylinder miller was sealed and rotated at 120 rpm for 30 minutes to form a uniform slurry.

70 grams of fine, sieved wheat flour and 7 grams of yeast cells were then gradually added into the slurry and battered in a blender to form a workable, plastic mixture.

A. Sample without Extrusion

The mixture was then divided equally, without extrusion, and placed in four Teflon coated petri dishes without sealing. These petri dishes were then transferred to a temperature controlled incubator at 28~30° C. The time in the incubator was varied four times from 15 minutes to 1 hour, with 15 minutes increments. At the end of each stage one of the petri dishes was gradually lowered into liquid nitrogen to stop the biological reaction and to prepare for the next step process.

The excess water was subsequently removed from the sample for 2 hours in a freeze-drying chamber at 20° C. and at a pressure of $10^{-1}$ to $10^{-3}$ mm Hg. The dried sample was then stabilised in a furnace at 200° C. for 30 minutes. The formatted samples were then gradually heated in a furnace at the rate of 5° C. per minute and held at 1000° C. to remove the organic additives. Subsequently, the samples were annealed at 1250° C. for two hours and gradually cooled to room temperature at the rate of 5° C. per minute.

Optical microscope examination of the porous structure of each of the sintered samples revealed that they all exhibited a porous structure almost identical to human cancellous bone. The pore and interconnected pore size gradually increased as the incubation time was increased, as shown in Table 1.

| Time | Pore Size | Interconnected Pore Size |
| --- | --- | --- |
| 15 minutes | 50~100 μm | Ave. Diam. 40 μm |
| 30 minutes | 300~500 μm | Ave. Diam. 200 μm |
| 45 minuteS | 800~1000 μm | Ave. Diam. 400 μm |
| 60 minutes | 2000~3000 μm | Ave. Diam. 1000 μm |

B. With Extrusion

After the mixing procedure the mixture was progressed through an extrusion unit to form a cylinder shaped specimen. The front mould of the extrusion unit was two connected cylinders, the diameters were 5 cm and 3 cm for the first stage and second stage cylinders, respectively. A steel net with 3 mm mesh was attached at both ends of the second stage cylinder. The extruded mixture was then placed on a Teflon coated plate without sealing. The plate, with its mixture, was then transferred to a temperature-controlled incubator at 28~30° C. for 30 minutes. Then the mixture was transferred to a refrigerator at −5° C. for 2 hours and subsequently the excess water was sublimated from the sample for 2 hours in a freeze-drying chamber at 20° C. and at a pressure of $10^{-1}$ to $10^{-3}$ mm Hg. The formatting, burning and annealing processes were the same as those described in section A. The sample showed a uniform tube-like porous structure with pore sizes ranging from 800 to 1000 μm long and an average diameter of around 200 μm. The interconnected pores, average diameter around 200 μm, connected at the ends of these tube-like macropores. The structure is ideal for osteoingrowth and the induction of vascularisation.

C. With Sealed Moulding

The extrusion process was the same as that described in section B. However, the steel net was removed during the extrusion process. The extruded cylinder shaped sample was transferred into a sealed cylinder mould. The incubation procedure and the sublimation process were the same as those described in section B, and the formatting, burning and annealing processes were the same as those described in section A. A cross section of the sample revealed a structure similar to that of human long bone. A compact structure formed the outer shell of the samples; it consisted of a hard, virtually solid mass made up of Ca/P ceramic arranged in concentric layers. A porous structure, similar to that found in cancellous/spongy bone, was found in the middle of the samples; the pore size gradually reduced and finally joined with the compact structure.

EXAMPLE 2

Sample of the porous HA product obtained in Example 1B were immersed in boiling HA slurry with an average particle size of 0.2 μm. The immersion times were from 30 minutes to 90 minutes with a 30 minutes interval and the slurry was stirred constantly. Afterwards the excess slurry was removed by a centrifuge process (from 2500 to 15000 rpm). The samples were subjected to the annealing process at 1280° C. for 5 hours.

Figure 2:
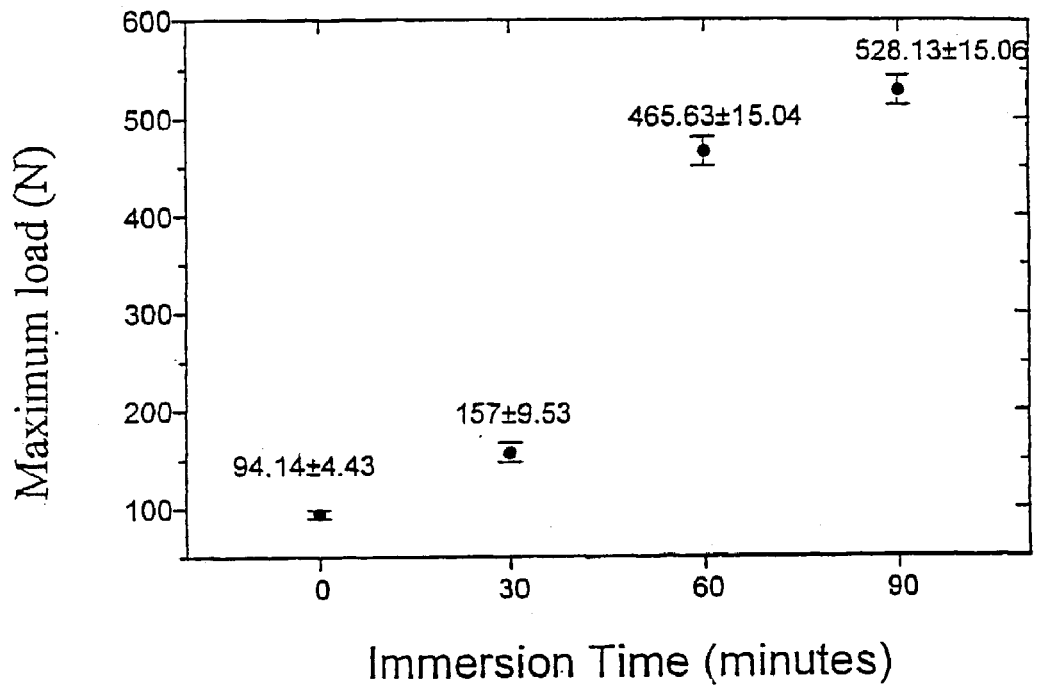
FIG. 2 is a graph comparing load values over time.

A mechanical test of the samples was carried out using a Lloyd bench-top test machine fitted with a 2.5 kN load cell and a remote computer controlled unit. The load was applied to the specimens (average sample contact area is 0.8 $cm^2$) with a crosshead speed of 0.1 mm per minute until brittle failure occurred. The results obtained are shown in FIG. 2. It can be seen that the compressive strength of the porous HA samples is increased as the immersion time increases.

EXAMPLE 3

6 grams of PCL was melted in a 150 cc glass beaker by placing it in a 60° C. oven. After the solid PCL had melted to a clear sticky fluid, 20 ml acetone was added to dissolve the PCl and form a fluent solution. The viscosity of the solution was 0.8835±0.025 pas. Porous samples of Example 1B were then immersed in the solution and kept at boiling by placing it on a hot plate at constant temperature of 57° C. After 20 minutes, the samples were removed and subjected to a centrifuge process (from 2500 to 15000 rpm) to remove any excess solution from the interconnected macroporous structure. The samples were then placed in a 60° C. oven to melt any blocking PCL in the macroporous structure and the centrifuge process was repeated.

Figure 3:
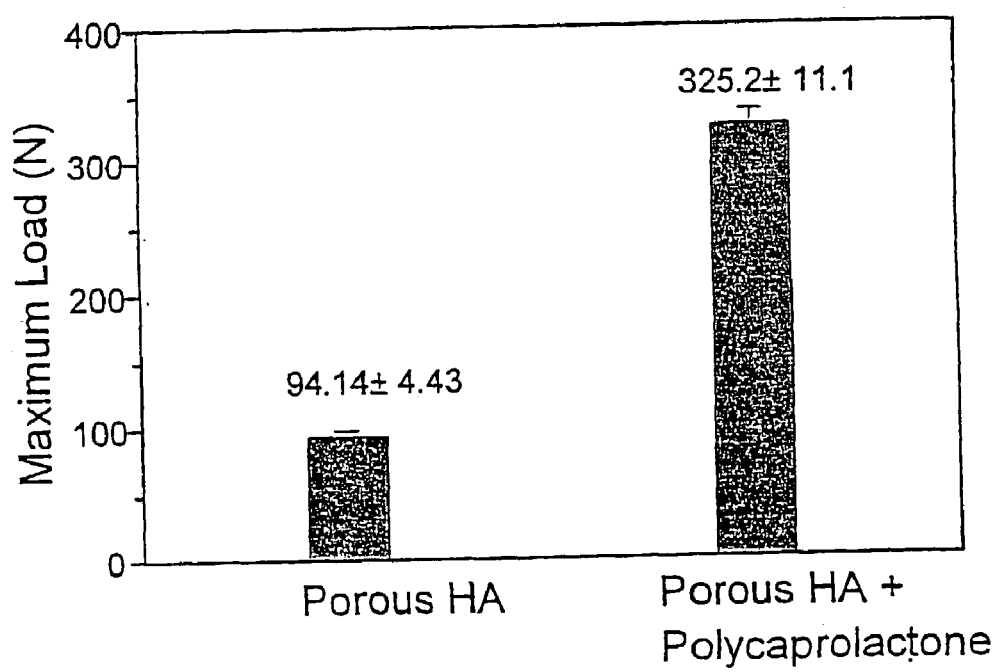
FIG. 3 is a chart comparing compressive strength versus material.

The mechanical test of Example 2 was carried out. The results obtained as shown in FIG. 3. It can be seen that the PCL reinforced porous HA samples had a significantly increased compressive strength.

The porous properties of the tested samples, measured according to ASTMC134 standard, before the immersion processes, were as following.

| Porosity of the tested porous HA samples | |
|---|---|
| Total volume, $cm^3$ | 1.06078 ± 0.01493 |
| Volume of open pores, $cm^3$ | 0.79737 ± 0.01935 |
| Volume of impervious pores, $cm^3$ | 0.20262 ± 0.00596 |
| Apparent porosity, P % | 79.6589 ± 0.28677 |
| Water absorption, A % | 133.81 ± 1.89755 |
| Apparent specific gravity | 2.93957 ± 0.03229 |
| Bulk density, $g/cm^3$ | 0.59597 ± 0.0074 |

The invention claimed is:

1. Process for preparing artificial bone which comprises:
   (i) preparing a mixture of a finely divided bio-compatible ceramic powder, an organic binder and a pore-forming agent in an inert liquid to form a body and causing at least some of the yeast to align along a common axis,
   (ii) optionally shaping the resulting body,
   (iii) allowing the yeast to form a porous structure in the body,
   (iv) heating the shaped body to a temperature sufficient to fix the porous structure, and
   (v) further heating the body to eliminate residues of organic binder and yeast and to fuse it.

2. Process according to claim 1 wherein the ceramic powder is of calcium phosphate.

3. Process according to claim 2 wherein the ceramic powder is α or β tricalcium phosphate.

4. Process according to claim 2 wherein the calcium phosphate is hydroxy apatite.

5. Process according to any one of claims 1 in which the powder has an average particle size not exceeding 100 microns.

6. Process according to any one of the preceding claims 1 in which the organic binder is a carbohydrate powder.

7. Process according to claim 6 in which the organic binder is corn flour or wheat flour.

8. Process according to claim 1 in which the inert liquid is water.

9. Process according to claim 1 wherein a slurry of the ceramic powder is first obtained and the organic binder and yeast are added thereto.

10. Process according to claim 9 in which the slurry of the ceramic powder is obtained with milling, optionally with a milling aid.

11. Process according to claim 9 in which a dispersing agent is incorporated with the ceramic powder.

12. The process according to claim 11 in which the dispersing agent is selected from the group consisting of an ammonia solution, orthophosphoric acid, an acrylic acid polymer, and a methacrylic acid polymer.

13. The process according to claim 9 wherein the organic binder and yeast are homogeneously dispersed in the slurry in a sealed oxygen-containing chamber.

14. The process according to claim 1 wherein the yeast is aligned in step (i) by extruding the body.

15. The process according to claim 1 in which the body is shaped using a mould.

16. The process according to claim 15 wherein the inert liquid is water and the mould is cooled to below the freezing point thereby to enhance the porous structure of the body.

17. The process according to claim 1 wherein after step (ii) inert liquid is removed from the body.

18. The process according to claim 1 wherein step (iv) is carried out a temperature from 100 to 230° C.

19. The process according to claim 1 wherein step (iv) involves subjecting the article to steam.

20. The process according to claim 1 wherein step (v) is carried out by heating to 400 to 1000° C. at a rate not exceeding 100° C. per minute.

21. The process according to claim 1 wherein after step (v) the body is annealed at a temperature up to 1450° C.

22. The process according to claim 1 wherein the product of step (v) is immersed in a ceramic slurry which is then boiled and the resulting body is removed by centrifuge.

* * * * *

UNITED STATES PATENT AND TRADEMARK OFFICE
CERTIFICATE OF CORRECTION

PATENT NO. : 7,094,371 B2
APPLICATION NO. : 10/343482
DATED : August 22, 2006
INVENTOR(S) : Wei Jen Lo It is certified that error appears in the above-identified patent and that said Letters Patent is hereby corrected as shown below:

Column 10, line 26:
At claim 1, replace "Process" with --A process--, and replace "pore-forming agent" with --yeast--.

Column 10, line 39:
At claim 2, replace "Process" with --The process--, and "is of" with --comprises--.

Column 10, line 41:
At claim 3, replace "Process" with --The process--.

Column 10, line 44:
At claim 4, replace "Process" with --The process--.

Column 10, line 46:
At claim 5, replace "Process" with --The process-- and replace "any one of claims" with --claim--.

Column 10, line 49:
At claim 6, replace "Process" with --The process--, and replace "any one of the preceding claims" with --claim--.

At each of claims 7, 8, 9, 10 and 11 replace "Process" with --The process--.
On The title page, item [57]
Replace the abstract with:

--A process for preparing artificial bone is described. One: (i) prepares a mixture of a finely divided bio-compatible ceramic powder, an organic binder and a pore-forming agent in an inert liquid to form a body and causes at least some of the pore-forming agent to align along a common axis; (ii) optionally shapes the resulting body; (iii) allows the pore-forming agent to form a porous structure in the body; (iv) heats the shaped body to a temperature sufficient to fix the porous structure and; (v) further heats the body to eliminate residues of organic binder and pore-forming agent and to fuse it.--

UNITED STATES PATENT AND TRADEMARK OFFICE
CERTIFICATE OF CORRECTION

PATENT NO. : 7,094,371 B2
APPLICATION NO. : 10/343482
DATED : August 22, 2006
INVENTOR(S) : Wei Jen Lo Page 2 of 2

It is certified that error appears in the above-identified patent and that said Letters Patent is hereby corrected as shown below:

At column 2, line 23 replace "humane" with --human--.

Signed and Sealed this

Sixth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,094,371 B2
APPLICATION NO. : 10/343482
DATED : August 22, 2006
INVENTOR(S) : Wei Jen Lo It is certified that error appears in the above-identified patent and that said Letters Patent is hereby corrected as shown below:

On the title page:
    Replace the abstract with:

--A process for preparing artificial bone is described. One: (i) prepares a mixture of a finely divided bio-compatible ceramic powder, an organic binder and a pore-forming agent in an inert liquid to form a body and causes at least some of the pore-forming agent to align along a common axis; (ii) optionally shapes the resulting body; (iii) allows the pore-forming agent to form a porous structure in the body; (iv) heats the shaped body to a temperature sufficient to fix the porous structure and; (v) further heats the body to eliminate residues of organic binder and pore-forming agent and to fuse it.--

At column 2, line 23 replace "humane" with --human--.

Column 10:
    At claim 1, replace "Process" with --A process--, and replace "pore-forming agent" with --yeast--.

Column 10:
    At claim 2, replace "Process" with --The process--, and "is of" with --comprises--.

Column 10:
    At claim 3, replace "Process" with --The process--.

Column 10:
    At claim 4, replace "Process" with --The process--.

Column 10:
    At claim 5, replace "Process" with --The process-- and replace "any one of claims" with --claim--.

Column 10:
    At claim 6, replace "Process" with --The process--, and replace "any one of the preceding claims" with --claim--.

UNITED STATES PATENT AND TRADEMARK OFFICE
CERTIFICATE OF CORRECTION

PATENT NO. : 7,094,371 B2
APPLICATION NO. : 10/343482
DATED : August 22, 2006
INVENTOR(S) : Wei Jen Lo It is certified that error appears in the above-identified patent and that said Letters Patent is hereby corrected as shown below:

Column 10:
    At each of claims 7, 8, 9, 10 and 11 replace "Process" with --The process--.

Signed and Sealed this

Thirteenth Day of November, 2007

JON W. DUDAS
*Director of the United States Patent and Trademark Office*